United States Patent [19]

Bambeck et al.

[11] Patent Number: 4,975,174
[45] Date of Patent: Dec. 4, 1990

[54] VERTICAL GEL ELECTROPHORESIS DEVICE

[76] Inventors: Gregory S. Bambeck, 2708 St. Elmo Ave., Canton, Ohio 44714; Kenneth R. Sibley, 2408 Benton St., Akron, Ohio 44312

[21] Appl. No.: 292,771
[22] Filed: Jan. 3, 1989
[51] Int. Cl.⁵ ............... G01N 27/26; G01N 27/28; B01D 57/02
[52] U.S. Cl. ............... 204/299 R; 204/182.8
[58] Field of Search ........... 204/299 R, 182.8, 182.9, 204/182.7

[56] References Cited

U.S. PATENT DOCUMENTS 3,208,929  9/1965  Raymond et al. ............ 204/299 R
4,325,796  4/1982  Hoefer et al. ............... 204/299 R X
4,707,233  11/1987  Margolis .................... 204/299 R X
4,773,984  9/1988  Flesher et al. .

Primary Examiner—John F. Niebling
Assistant Examiner—John S. Starsiak, Jr.

[57] ABSTRACT

Vertical gel electrophoresis devices comprising a bottom tank having an electrode associated therewith, a top tank insertable into said bottom tank, the top edge of the top tank extending no higher than the top edges of the bottom tank, and a cover assembly including a lid adapted to be placed on top of said bottom tank and a second electrode. As a safety feature, the second electrode is fixedly associated with the cover assembly so that it is removed when the cover assembly is removed. The device also includes an interlock arrangement so that the cover assembly cannot be inserted in place or removed by a simple vertical motion unaccompanied by a horizontal motion.

10 Claims, 4 Drawing Sheets

VERTICAL GEL ELECTROPHORESIS DEVICE

TECHNICAL FIELD

This invention relates to vertical gel electrophoresis devices.

BACKGROUND ART

Electrophoresis involves the separation of charged molecular species in a molecular field. An electric field is applied to a macromolecule mixture, causing the mixture to be separated into fractions. Gel electrophoresis involves the migration of charged macromolecules through a porous gel under an applied electric field. Electrophoresis occurs because of differences in mobility of the different molecular species in the gel. Usually separation is based on differences in molecular weight, but can be based on differences in some other parameter, such as the isoelectric points of the molecular species. Gel electrophoresis may be used for either analytical or preparative purposes, and is more frequently used for the former.

Gel electrophoresis devices may be broadly categorized as vertical gel electrophoresis devices or as horizontal gel electrophoresis devices. The former have a number of advantages over the latter. This invention is concerned with vertical gel electrophoresis devices.

Representative vertical gel electrophoresis devices are shown in U.S. Pat. Nos. 4,325,796 to Hoefer et al., and 4,707,233 to Margolis. Both devices include a bottom tank and a top tank removably situated inside the bottom tank so as to provide two spaces for electrolytes, i.e., a first (or lower) space between the respective walls of the bottom and top tanks and a second (or upper) space inside the top tank. Both include a vertically extending gel receptacle or cassette which contains a gel for separation of a macromolecule mixture. In both devices, the only intended path for electricity is from an electrode in the top space or compartment to an electrode in the bottom space or compartment, via an electrolyte in the top space, the gel and an electrolyte in the bottom space, in that order.

Various problems are associated with known vertical gel electrophoresis devices. One is that most are structurally complex, and there has been an increasing tendency toward complexity with the development of the art. Another is that a tight seal must be maintained between the top and bottom compartments. This requires the use of a fluid tight gasket. Failure to maintain this tight seal may result in short circuiting, and electrolyte running out of the top compartment. Devices of both U.S. Pat. Nos. 4,325,796 and 4,707,233 require fluid tight seals between the top and bottom compartments. Some devices pose safety hazards during assembly or disassembly because both electrodes or connectors connected thereto become exposed.

Further disadvantages of the device of U.S. Pat. No. 4,325,796 include the use of clamps or screws to position the vertical gel cassettes, and a construction which makes short circuiting possible if the top compartment is overfilled with electrolyte. Adjusting clamps or screws are very undesirable because they may be overtightened, which could result in breakage of the glass forming the side walls of the cassette. Overfilling of the top compartment in this device could cause short-circuiting because of the large cross-sectional area between the respective side walls of the top and bottom tanks. If such short-circuiting should occur, the heat generated would be enough to evaporate substantial quantities of electrolyte. This could break the electrical circuit and terminate a run.

Disadvantages of the device of U.S. Pat. No. 4,707,233 include use of porous membranes in addition to the gel, and the presence of a free space between the membranes. The membranes, typically made of paper impregnated with a suitable gel, are fragile. The free recovery space provides a space in which macromolecules are collected and this space requires special efforts for cleaning. Also, both electrodes are associated with the top tank (on opposite sides of the bottom wall thereof), so that their respective connectors (not shown) could remain plugged into an external power source even after the top tank has been removed, with serious safety consequences.

DISCLOSURE OF THE INVENTION

The present invention provides an electrophoresis device which is simple, inexpensive, safe and reliable.

The present device is so constructed that it is virtually impossible for both electrodes to be connected to an external power supply unless the device is fully assembled. Other features of the device of this invention are as follows: it employs no clamps or clamping screws that require adjustment by the user; it is very unlikely to "run dry" unless the user fails to adequately fill both compartments with electrolyte in the first place; it will function properly even in the absence of a tight seal between the upper and lower electrolyte compartments; and it employs an interlock so that the top cover cannot be inserted in place or removed by a simple vertical motion.

The electrophoresis device of this invention is a vertical gel electrophoresis device comprising:

(a) a bottom tank comprising a bottom wall and side wall means, and which is open at the top;

(b) a top tank removably situated inside said bottom tank, said top tank comprising a bottom wall and side wall means, the depth of said top tank being appreciably less than the depth of said bottom tank so as to provide a first compartment for electrolyte between the respective walls of the bottom and top tanks and a second compartment inside said top tank, side wall dimensions of the top tank being slightly smaller than those of the bottom tank so as to provide a slight clearance between the side wall means of the top tank and the side wall means of the bottom tank;

(c) a removable top cover for enclosing said electrophoresis device;

(d) first electrode means fixedly associated with said bottom tank and including a first electrode in said first compartment;

(e) second electrode means including a second electrode in said second compartment;

(f) a vertical gel cassette open at the top and bottom and extending through an opening in the bottom wall of said top tank; and (g) interlock means for preventing removal of said cover by vertical lifting unaccompanied by horizontal motion.

BEST MODE FOR CARRYING OUT THE INVENTION

Figure 1A:
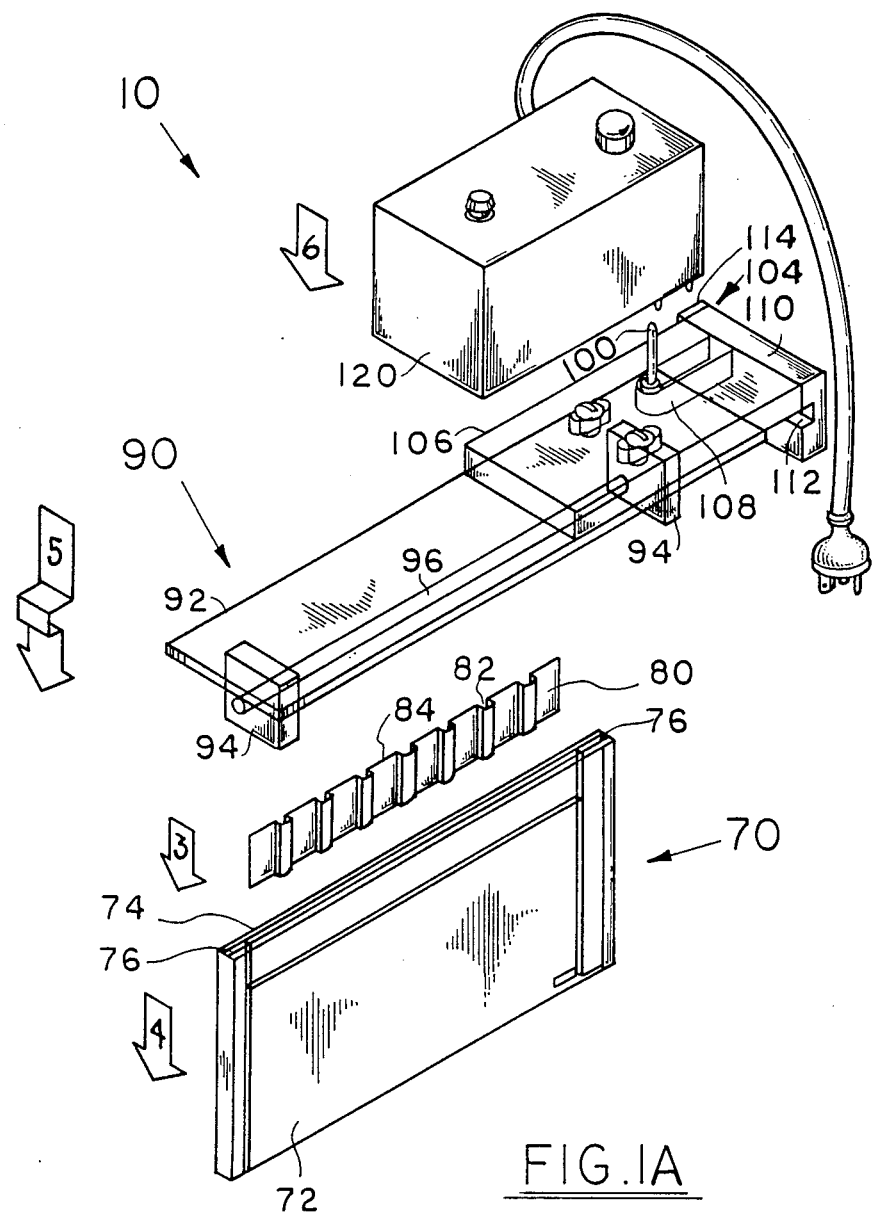
FIGS. 1A and 1B together form FIG. 1, which is an exploded view of the electrophoresis device of this invention.

This invention will now be described with particular reference to the best mode and preferred embodiments thereof, as illustrated in the accompanying drawings.

Electrophoresis device 10 of this invention is a vertical gel electrophoresis device which is made of "Plexiglas" or "Lucite." (Both "Plexiglas" and "Lucite" are registered trademarks.)

All parts forming device 10 are preferably made of such clear, transparent plastic, except as otherwise noted hereinafter.

Device 10 includes a bottom tank 20, which is an open-top, hollow, rectangular prism having a bottom wall 22, front wall 24, back wall 26, and left and right side walls 28 and 30, respectively. Bottom wall 22 is horizontal and the front, back and side walls are vertical. An additional vertical plate 32 is bolted to the outside of right side wall 30. Walls 30 and 32 preferably have the same width, height and thickness, and are aligned so that their corresponding edges coincide. A horizontal rectangular block 33, which is just slightly wider than the combined thicknesses of walls 30 and 32, rests on top of the top edges of walls 30 and 32.

Inside the bottom tank 20 are a pair of vertical cassette guide rails 34. Each of these guide rails is in the form of a vertical plate, extending upwardly from the bottom of bottom tank 20 to a height slightly greater than ½ that of the bottom tank. Each of the guide rails 34 has a vertical groove or slot 36 which terminates above the bottom of tank 20, at a height which corresponds to that of the bottom edge of the vertical gel cassette to be described later. Slots 36 form guide runners for the gel cassette.

Top surfaces 38 of cassette guide rail plates 34 form support surfaces for the top tank (to be described later) of device 10.

Cassette guide rail plate 36 are spaced inwardly from the side walls 28–30 of device 10 by spacers 40 which rest on the bottom wall 22 of device 10.

A first electrode 42, preferably made of graphite, extends horizontally through the space inside bottom tank 20 a short distance above the bottom wall thereof. The ends of electrode 42 are supported by spacers 40 and cassette guide rail plates 34. A first buffer solution, which is electrically conductive, surrounds the electrode 42 when the device 10 is in operation.

A vertical conductor 44, which is embedded in vertical plate 32, and a prong or banana plug 46, provide an electrically conductive path from electrode 42 to an external power supply.

The bottom tank electrode 42 is normally the anode.

At the top of left side wall 28 of bottom tank 20 is a groove assembly 48 formed by a vertical block 50, a horizontal block 52 adhered to the top edge of vertical block 50 and extending inwardly therefrom, and a pair of thin, square, vertical end plates 54. (The front end plate 54 is not shown in FIG. 1.) The depth (from front to back) of blocks 50 and 52 is approximately the same as the depth (from front to back) of side wall 28. The lower portion of vertical block 50 is joined to the outside of side wall 28. The lower surface of horizontal block 52 is spaced from the top edge of side wall 28 so as to form a groove or slot 56 for a lid or cover to be described later. End plates 54, which are joined to the front and back edges of blocks 50 and 52, form the side walls of groove 56 and prevent the cover or lid from being inserted in place or removed from its position atop side wall 28 by a simple horizontal motion.

Figure 4A:
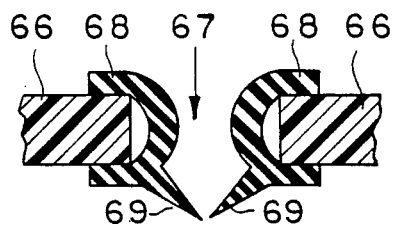
FIG. 4A is a fragmentary vertical sectional view of a preferred sealing gasket for the vertical gel cassette.
Figure 4B:
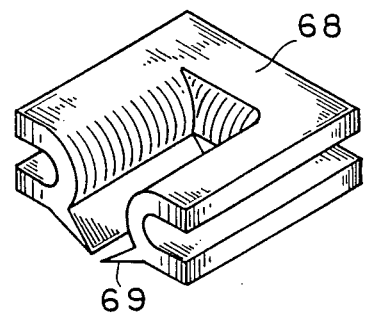
FIG. 4B is a fragmentary isometric view of the preferred sealing gasket for the vertical gel cassette of this invention.

Device 10 has a top tank 60 in the form of an open top, hollow, rectangular prism having front wall 62, back wall 63, and a pair of side walls 64. The top edges of top tank 60 are no higher than, and are preferably slightly lower than the top edges of bottom tank 20. Top tank 60 also has a bottom wall 66, which has a central longitudinal opening 67 in the form of a long, thin, rectangular slot. An elastomeric gasket 68, preferably made of rubber similar to that used in windshield wipers, extends around the perimeter of opening 67. This gasket is shown in detail in FIGS. 4A and 4B. Each of the four sides of this gasket is a "U" shaped cross-section, with the curved portion of the "U" overlying the edges of opening 67. Gasket 68 preferably has a pair of lips 69 extending downwardly and inwardly along the two long sides (preferably not along the two short sides) of the gasket 68.

A vertical gel cassette 70 (to be described in detail later) extends through opening 67 and lips 69 engage the side walls of the cassette 70. The construction of lips 69 is such that the amount of electrical leakage between the lip 69 and the cassette side walls 70 does not exceed the current passing through the cassette 70.

The external cross sectional area of top tank 60 is only slightly smaller than the internal cross sectional area of bottom tank 20, both being measured on a horizontal plane near the top of the device 10. It is important that there be only a small clearance between the vertical walls 62, 63 and 64 of top tank 60 and the corresponding vertical walls 24, 26, 28 and 30 of bottom tank 20. In a representative device 10, 24.6 cm wide and 5.0 cm thick (the size illustrated in Table I below) the annular space between top tank 60 and bottom tank 20 should be no more than about 3 to 4 mm on any one side preferably no more than about 2 mm on any one side. In terms of cross sectional area, the cross sectional area of the annular space should be no more than about ⅓ preferably not more than ¼ the cross sectional area of top tank 60. The resulting small cross sectional area makes impossible any significant or deterimental current flow through this annular space even in the event that the top tank is overfilled with electrolyte. Dimensions of the device 10 of this invention are such that combined electrial leakage current in the vicinity of gasket 69 and through the annular space between tanks 20 and 60 cannot exceed about four times the current flowing through the gel cassette 70 assuming that the gel in cassette 70 and the buffer solutions have equal conductances. Thus, the total leakage current cannot exceed about 260 milliamperes and is preferably less, when the current through the gel cassette is 65 milliamperes. In the event of larger or smaller currents through the gel cassette, the allowable leakage current will be proportionally larger or smaller.

Figure 3:
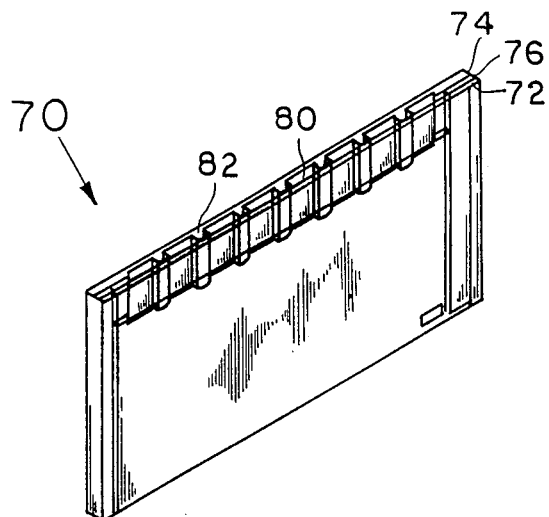
FIG. 3 is an isometric view of a vertical gel cassette for use in the device of the present invention.

Vertical gel cassette 70, best seen in FIGS. 1A and 3, is open at the top and bottom and comprises front plate 72, back plate 74 and spacers 76 at the sides thereof. The front and back plates 72, 74, respectively are preferably made of glass. The gel cassette 70 may be held together by strips of vertically extending adhesive tape (not shown) which overlay the outside surfaces of spacer 76 and the vertical side edges of plates 72 and 74. The interior space of gel cassette 70 (except for the top portion thereof) is filled with a suitable electrophoresis gel before the device 10 is put into operation. The top portion which is not filled with gel constitutes about 15 to about 25 percent of the total height of cassette 70.

Inside the upper portion of gel cassette 70 is a vertical comb 80. Comb 80 is preferably in the form of a one piece, thin, translucent or opaque plastic sheet, e.g., polystyrene, which is formed from a thin, flat, rectangular, plastic sheet and which as formed, has a plurality of thinly spaced parallel ridges 82. These ridges form the boundaries of lanes or channels for macromolecule samples to be fractionated. Comb 80 is more fully described in applicants' co-pending U.S. patent application Ser. No. 07/240,540, filed Sept. 6, 1988. Between adjacent ridges 82 are flat portions 84. Top surfaces of ridges 82, which are preferably slightly convex, abut against the front plate 72, while the flat portions 84 abut against the back plate 74. The top edge of comb 80 is just slightly lower than the top edges of plates 72 and 74.

Figure 2:
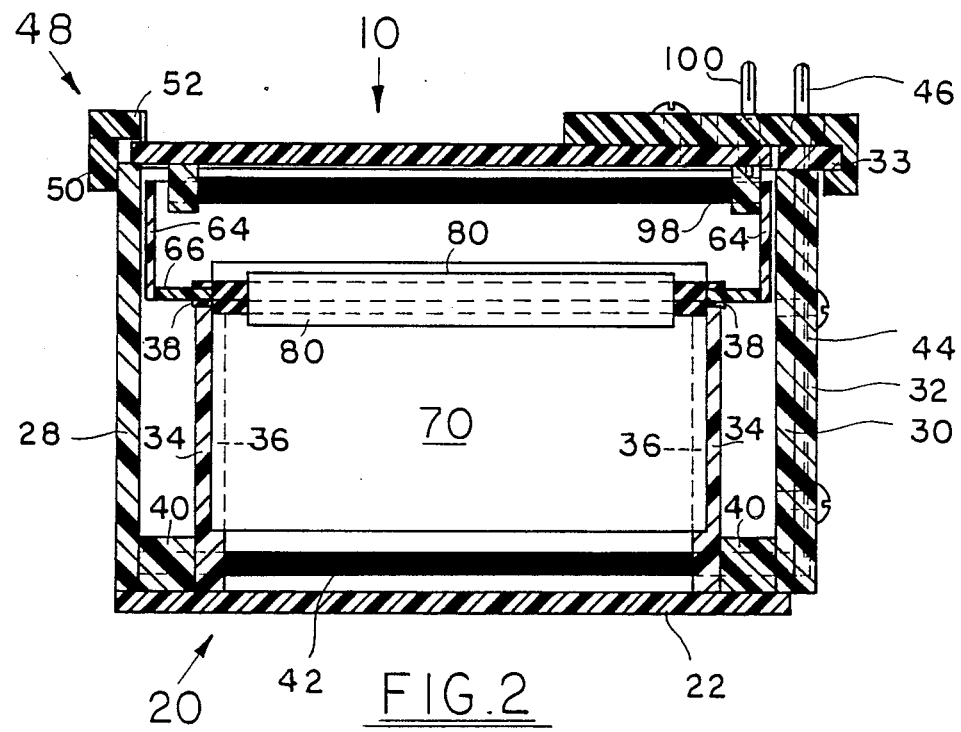
FIG. 2 is a vertical sectional view, taken along line 2—2 of FIG. 1B.

Electrophoresis device 10 also includes a cover assembly 90, shown in FIGS. 1A and 2. Cover assembly 90 comprises a horizontal, rectangular lid or cover 92. The width (which is the longest dimension) of cover 92 is substantially equal to the width of the interior space of the bottom tank 20 (i.e., the distance between the insides of wall 28 and 30). A pair of depending vertical blocks 94, depending from the underside of cover 92 near the side edges thereof, support the ends of the second electrode (which is normally the negative electrode or cathode) 96. Electrode 96 is preferably made of graphite. A vertical metallic conductor 98 (see FIG. 2) extends upwardly from electrode 96 and terminates in an upwardly extending metallic prong or banana plug 100. The distance between depending vertical blocks 94 is slightly less than the interior width of the top tank 60, so that blocks 94 extend into the interior space of the top tank when device 10 is assembled. An interlock assembly 104 on the right hand side of cover assembly 90 is formed by a horizontal plate 106 which is bolted to the top surface of lid 92, which extends laterally beyond lid 92 and vertical wall member 32, and which has a U-shaped cut-out portion 108 to permit banana plugs 46 and 100 to extend therethrough; a notched vertical plate 110 joined to the outer edge of plate 106 and having a horizontal slot or notch just below the bottom surface of plate 106; and a pair of vertical end plates 114 which enclose the sides of slot 112. The front end plate 114 is not shown in FIG. 1A.

A power converter 120 is supplied for converting alternating current (AC) (usually 110 or 120 volts in the United States) in the external power supply to direct current (DC) (preferably 110 to 250 volts) for use in the electrophoresis device 10. Converter 120 includes a rectifier, and usually a transformer and may also include a capacitor. Suitable devices for this purpose are known in the art.

Dimensions of electrophoresis device 10 and its component parts may be varied in accordance with the needs of the user. The dimensions of bottom tank may vary widely, from a few millimeters, to one meter or more on each side. However, the thickness of the interior space of gel cassette 70 should not exceed about 3 mm because thicker gel masses result in heating which results in loss of precision. Representative dimensions are shown in table I below. These dimensions illustrate a device having a gel cassette with internal thickness of 1.5 mm, which is the most common gel cassette internal thickness currently in use. All dimensions shown below are measured as follows: width is measured from side to side, depth is measured from front to back, and height is measured vertically. All dimensions are given in centimeters.

TABLE I

Representative Dimensions

| Part | Width cm | Height cm | Thickness cm |
| --- | --- | --- | --- |
| Bottom tank 20 | | | |
| Exterior | 24.6 | 14.0 | 5.0 |
| Interior | 22.8 | 13.5 | 3.9 |
| Top tank 60 | | | |
| Exterior | 22.5 | 4.0 | 3.7 |
| Interior | 21.7 | 3.7 | 3.2 |
| Gel cassette 70 | | | |
| Exterior | 18.0 | 9.0 | 0.6 |
| Interior | 16.0 | 9.0 | 0.15 |
| Precast gel | 16.0 | 7.0 | 0.15 |
| Comb 80 | 15.0 | 2.0 | 0.16 |

An electrophoresis device 10 having one gel cassette 70 has been shown for purposes of illustration. The device may have two or more gel cassettes (as many as desired). When two cassettes are present, they may be arranged one behind the other. The thickness and the width of device 10 may be varied to accommodate the desired number of gel cassettes.

Gels used in the electrophoresis device of this invention may be conventional. For example, a polyacrylamide gel cross-linked with bis-acrylamide may be used for separation of protein mixtures according to molecular weight. Such gel may contain, for example, about three to about 30 weight percent acrylamide, balance essentially water, with additional ingredients such as buffering agent constituting only a small percentage of total weight. Protein mixtures which can be separated with such a gel may have a molecular weight range from as low as 3,000 daltons to as high as two million daltons. A urea type gel may be used for separation of DNA from RNA. Still other types of gels may be used for separation of protein mixtures according to isoelectric point. Suitable electrophoresis gels and methods for preparing the same are known in the art, and so further details will not be given here. The electrical conductivity of the buffer solutions (which are normally of the same composition at the outset of a run) is about the same or just slightly higher than the electroconductivity of the gel. Normally, the electrical conductivity of the gel is the current-limiting factor in the device 10.

The gel is preferably prepared in precast form, having a width and thickness (or depth) equal to those of the interior space of the gel cassette 70, and a height slightly less than that of the gel cassette.

The gel (preferably precast) is inserted into the interior space of the gel cassette 70 by means known in the art, prior to assembly of the electrophoresis device 10. The gel should be charged to the gel cassette so that the bottom edge of the gel coincides with the bottom edge of a cassette. For instance, in the illustration in table I, the height of the gel cassette is 9 cm and the height of the gel is 7 cm, leaving a 2 cm air space at the top of the cassette.

Figure 1B:
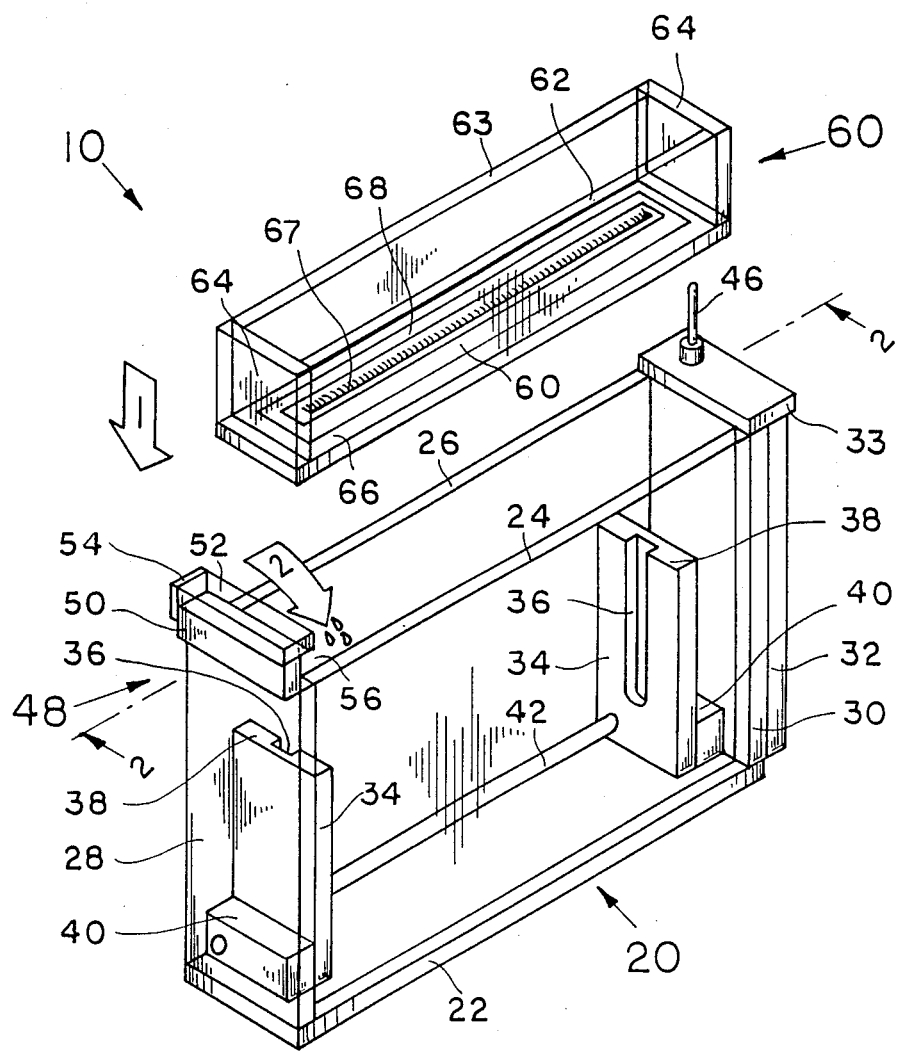

Assembly of the device 10 is illustrated in FIG. 1, in which numerals inside the open arrows indicate the sequence of steps.

First, top tank 60 is inserted into the bottom tank 20, top tank 60 (particularly gasket 68 thereof) will rest on the top surfaces 38 of guide rails 34. When the top tank 60 is in place, the interior space of the device 10 is divided into two spaces or compartments, i.e., a first space which is between the respective walls of the bottom tank 20 and the top tank 60 (i.e., primarily below bottom wall 66 of top tank 60) and a second space or compartment which is inside the top tank 60 (i.e., above the bottom wall 66 of top tank 60 but below the top edge of the top tank).

Second, a first running buffer solution is charged to the first compartment of the device by pouring it into the top tank and allowing it to flow through opening 67 into the first space or compartment. Addition of buffer is stopped when the liquid level reaches the bottom surface of bottom wall 66 of top tank 60.

Third, comb 80 is inserted into the free space at the top of cassette 70 so that the bottom edge of comb 80 rests lightly on the top surface of the gel. The comb is not pushed into the gel at this time.

Fourth, the comb and gel cassette assembly (80 and 70) is inserted into the top tank gasket 68 slowly, with a firm, gentle pressure. The user pushes the cassette assembly slowly downward with his or her thumbs until the gel cassette assembly is seated at the bottom of the cassette guide rail slots 36 in the bottom tank 20. Then additional running buffer is added until a liquid level just below (about 5 mm below) the top edges of top tank side walls 62, 63 and 64 is reached. A small amount of buffer solution leaks through to bottom tank 20 in the vicinity of gasket 68, as a result the buffer solution levels in top tank 60 and bottom tank 20 after filling are the same. Comb 80 is then pushed lightly into the gel at gel cassette 70, so that the bottom edge of the comb is about 2-3 mm below the top edge of the gel (the top edge of the comb will be about 2-3 mm below the top edge of cassette 70). The comb should be inserted so that the ridges 82 therein face the user.

Before proceeding further with assembly of device 10, the user flushes any air bubbles out of the sample well (the comparatively wide spaces between successive ridges 82) which may be present at the top of the gel surface, using running buffer solution and injecting the same with a Pasteur pipette or syringe. Care must be taken not to use too strong a stream of flow, as that could dislodge the gel surface from the comb or damage the gel surface.

After flushing, the user injects sample solutions to be fractionated into each of the sample wells (or as many sample wells as are needed, if the number of samples is less than the number of sample wells), using a microsyringe or micropipette. Suggested sample volume is about 10 microliters in each sample well, with a protein concentration of about 20 micrograms per microliter in each sample.

Assembly of electrophoresis device 10 is resumed after the macromolecule samples have been charged to the upper end of gel cassette 70.

The cover assembly 90 is put in place as the fifth step in the assembly operation. Banana plug 100, which is associated with the top tank electrode 96, is positioned so that it is adjacent to the bottom tank banana plug 46. This is usually to the user's right. Because of the interlock, it is not possible to lower the cover assembly 90 into place by a simple vertical motion. Instead, it is necessary to lower the cover assembly 90 into place by first lowering the left edge of lid 92 so that it rests on top of the vertical walls of lower tank 20 close to slot 56, with the right side of the assembly 90 at a slightly higher elevation, and then gently inserting the left edge of lid 92 into slot 56 (this requires a slight leftward motion of the assembly 90) while lowering the right side of assembly 90 into place so that the lid rests on the top edges of the vertical walls of bottom tank 20. This interlock is achieved by dimensioning the cover assembly 90 so that the horizontal distance from the left edge right hand surface of right hand block 94 is just slightly greater than the horizontal distance from the inside edge of block 52 to the inside surface of the right side wall 64 of top tank 60. As little as one millimeter of difference is sufficient. Cover assembly 90 is removed at the end of an electrophoresis run by a procedure which is the exact reverse of the assembly procedure. This interlock is a safety feature which prevents the user from casually inserting in place or removing the cover assembly 90 from partial assembly of bottom tank 20 and top tank 60. The fact that horizontal block 52 of groove assembly 48 is at a higher elevation than the top of bottom tank 20 makes it impossible to place the cover assembly 90 in the wrong orientation, i.e., with the two banana plugs 46 and 100 at opposite sides of the device 10.

Finally, the sixth and last step of assembly is to place the converter on top of the cover assembly 90, with the jacks (not shown) of the converter 120 receiving the banana plugs 46 and 100. Converter 120 also has an on/off switch (not shown). This switch is turned "on" when the user is ready to begin an electrophoresis run.

During an electrophoresis run, current flows from the anode 42 through the first buffer solution (in lower tank 20), the gel in gel cassette 70, the second buffer solution (in upper tank 60) to the anode 96, thence back through converter 120 to the external power supply. (By convention, current flows from the positive to the negative terminal; the actual flow of electrons is in the opposite direction, as is well known.)

Electrophoresis may be carried out at either constant voltage or constant current. The apparatus described is designed for constant voltage; by choice of a suitable converter 120, constant current operation is possible. When constant voltage is used, current diminishes as the run continues; when constant current is utilized, the applied voltage must be increased as the run progresses.

When the electrophoresis run is completed, the current is switched off (at the on/off switch in converter 120), and the device 10 is disassembled in the reverse order in which it was assembled except that the gel cassette 70 should be pushed downwardly until it is free of top tank 60. (The downwardly pointing angle of wiper blades 69 of gasket 68 make it undesirable to push the cassette upwardly to remove it from the top tank.) The gel in the cassette 70 may be removed and further processed by slitting the adhesive tape at one edge of cassette 70 with a knife and opening the cassette in the manner that one opens a book. The gel may be gently lifted from the cassette and further processed by means which are known in the art.

The electrophoresis device 10 of the present invention has several advantages over vertical electrophoresis devices presently known in the art. First of all, it is safe. Since one electrode assembly, i.e., anode 42 and its banana plug 46 are associated with the bottom tank 20, while the other electrode assembly, i.e., cathode 96 and its banana plug are associated with the cover assembly 90 and therefore removable with the cover assembly, it is virtually impossible for both electrodes or the conductors associated therewith (including the respective banana plugs 46 and 100) to be inadvertently connected to an external power supply when the device is not fully assembled, with the cover assembly 90 in place so that the device is enclosed. A further safety feature is that it is impossible for the device to "run dry." If the bottom compartment (inside the bottom tank 20 and below the top tank 60) is filled to the proper level as previously indicated in the first place, little or no buffer solution can run out of the second compartment (inside top tank 60) and the anode 96 will always be at least partially immersed in buffer solution. The small clearances between the respective vertical walls of the bottom and top tanks make short circuiting with attendant evaporation of buffer solution virtually impossible, even if the top tank is over filled with buffer solution. While the gasket 68 may provide a fluid tight fit around the sides and edges of the gel cassette 70, there is no harm even if it does not. Again, the cross sectional area of the solution path through buffer solution in vicinity of a gasket 68 which is not quite fluid tight, would be so small that no significant current flow via this route would take place, hence no short circuiting and no evaporation of solution. Another advantage of the device of this invention is that it is simple and hence inexpensive compared to other electrophoresis devices having similar capabilities. Furthermore, the absence of any clamps or clamping screws that the user must tighten and loosen, reduces considerably the chance for breakage of the glass walls of cassette 70 by overtightening. Top tank 60 is positioned solely by gravity and the small clearance between the respective vertical walls of top tank 60 and bottom tank 20. Cassette 70 is positioned by guide rail slots 36 and is held together by adhesive tape. No clamps or adjusting screws are needed in either case. Other advantages will be apparent to those skilled in the art.

While the present invention has been described with reference to the best mode and preferred embodiment thereof, it shall be understood that this description is by way of illustration and not limitation.

What is claimed is:

1. A vertical gel electrophoresis device comprising:
   (a) a bottom tank comprising a bottom wall and side wall means, and which is open at the top;
   (b) a top tank removably situated inside said bottom tank, said top tank comprising a bottom wall and side wall means, the depth of said top tank being appreciably less than the depth of said bottom tank so as to provide a first compartment for electrolyte between the respective walls of the bottom and top tanks and a second compartment inside said top tank, side wall dimensions of the top tank being slightly smaller than those of the bottom tank so as to provide a slight clearance between the side wall means of the top tank and the side wall means of the bottom tank;
   (c) a removable top cover for enclosing said electrophoresis device;
   (d) first electrode means fixedly associated with said bottom tank and including a first electrode in said first compartment and a conductor means associated with said first electrode;
   (e) second electrode means including a second electrode in said second compartment and conductor means associated with said second electrode;
   (f) a vertical gel cassette open at the top and bottom and extending through an opening in the bottom wall of said top tank; and
   (g) interlock means for preventing removal of said cover by vertical lifting unaccompanied by horizontal motion.

2. A device as claimed in claim 1 wherein said second electrode and the conductor means associated therewith are fixedly mounted with respect to said cover and insertable and removable therewith.

3. A device as claimed in claim 1 wherein said interlock means comprises means associated with said bottom tank for forming immediately above the top of one side wall of said bottom tank, a horizontally extending slot for receiving one side of said cover.

4. A device as claimed in claim 3 wherein said cover has depending therefrom a pair of non-conductive members for supporting said second electrode and wherein the horizontal distance from the edge of said cover insertable into said slot to the outer surface of the electrode support member which is remote from said edge is greater than the distance from the inmost edge of the means forming said slot to the inside surface of the side wall of said top tank which is remote from said means forming said slot, so that said cover cannot be put in place or removed by a simple vertical motion unaccompanied by horizontal motion.

5. A device as claimed in claim 1 wherein the conductor means associated with said first electrode are imbedded in a vertical wall of said bottom tank and terminate in a first upwardly extending conductive prong, and wherein the conductor means associated with said second electrode terminate in an upwardly extending second conductive prong.

6. A device as claimed in claim 1 wherein the top edge of said top tank is no higher than the top edge of said bottom tank.

7. A device as claimed in claim 1 wherein said bottom tank includes vertically extending guide rail means for positioning said vertical gel cassette.

8. A device as claimed in claim 1, further including a converter for converting alternating current to direct current, said converter being adapted to be placed above said cover and to receive the terminal portions of said conductor means.

9. A device as claimed in claim 1 wherein the clearance between the side wall means of the top tank and the side wall means of the bottom tank is sufficiently small so that the cross sectional area of the annular space between the side walls means of the top tank and the side wall means of the bottom tank is no more than about 25% of the cross sectional area of the top tank, when both cross sectional areas are measured in a horizontal plane.

10. A device as claimed in claim 1 wherein said top and bottom tanks are substantially filled with electrolyte and the interior space of said gel cassette is filled with an electrophoresis gel, and wherein the maximum possible leakage current is not more than about four times the amount of current passing through said gel.

* * * * *